United States Patent
Spiro et al.

(10) Patent No.: US 11,152,125 B2
(45) Date of Patent: Oct. 19, 2021

(54) AUTOMATIC VALIDATION AND ENRICHMENT OF SEMANTIC RELATIONS BETWEEN MEDICAL ENTITIES FOR DRUG DISCOVERY

(71) Applicant: International Business Machines Corporation, Armonk, NY (US)

(72) Inventors: Adam Spiro, Tel-Aviv (IL); Chen Yanover, Zichron Yaakov (IL)

(73) Assignee: International Business Machines Corporation, Armonk, NY (US)

( * ) Notice: Subject to any disclaimer, the term of this patent is extended or adjusted under 35 U.S.C. 154(b) by 155 days.

(21) Appl. No.: 16/432,961

(22) Filed: Jun. 6, 2019

(65) Prior Publication Data

US 2020/0388401 A1 Dec. 10, 2020

(51) Int. Cl.
*G16H 70/40* (2018.01)
*G06N 3/02* (2006.01)
(Continued)

(52) U.S. Cl.
CPC ............ *G16H 70/40* (2018.01); *G16H 20/10* (2018.01); *G16H 50/70* (2018.01)

(58) Field of Classification Search
CPC ........ G16H 50/70; G16H 10/60; G16H 50/20; G16H 20/10; G16H 70/40; G16H 70/60;
(Continued)

(56) References Cited

U.S. PATENT DOCUMENTS

| 2013/0179091 A1 | 7/2013 | Jackson et al. |
| 2017/0316175 A1 | 11/2017 | Hu et al. |
| 2018/0150605 A1* | 5/2018 | Co ........................ G10L 15/26 |

FOREIGN PATENT DOCUMENTS

WO WO-2017172629 A1 * 10/2017 ........... G06N 3/0481

OTHER PUBLICATIONS

Qu, X.A., Gudivada, R.C., Jegga, A.G. et al. Inferring novel disease indications for known drugs by semantically linking drug action and disease mechanism relationships. BMC Bioinformatics 10, S4 (2009). https://doi.org/10.1186/1471-2105-10-S5-S4 (Year: 2009).*

(Continued)

*Primary Examiner* — Elaine Gort
*Assistant Examiner* — Constantine B Siozopoulos
(74) *Attorney, Agent, or Firm* — Gregory J. Kirsch

(57) ABSTRACT

Embodiments of the present systems and methods may provide techniques that provide enrichment of semantic graphing with relations that can enable a higher resolution of the semantic relationships and enable a more accurate prediction of new relations in the graph. For example a method for drug discovery and drug repositioning may comprise generating semantic relationships, at the computer system, based on data relating to a plurality of aspects of drugs and pharmaceutical compounds, generated semantic relationships represented in the form of a semantic graph, learning, at the computer system, new relations among the semantic relationships in the semantic graph using Denoising Autoencoders to process the semantic graph, and generating, at the computer system, predictions for drug discovery and drug repositioning based on the semantic relationships, including the newly found relations.

18 Claims, 8 Drawing Sheets

(51) Int. Cl.
*G16H 20/10* (2018.01)
*G16H 50/70* (2018.01)

(58) Field of Classification Search
CPC ........ G16H 15/00; G06N 20/00; G06N 5/025; G06N 3/02; G06N 20/10
See application file for complete search history.

(56) References Cited

OTHER PUBLICATIONS

Wu, Y.; Wang, G. Machine Learning Based Toxicity Prediction: From Chemical Structural Description to Transcriptome Analysis. Int. J. Mol. Sci. 2018, 19, 2358. (Year: 2018).*

Sang, Shengtian, et al. "SemaTyP: a knowledge graph based literature mining method for drug discovery." BMC bioinformatics 19.1 (2018): 1-11. (Year: 2018).*

Fung et al. Semisupervised Learning Based Disease-Symptom and Symptom-Therapeutic Substance Relation Extraction from Biomedical Literature. Feng et al. Hindawi Publishing Corporation. BioMed Research International. vol. 2016, Article ID 3594937, 13 pages. http://dx.doi.org/10.1155/2016/3594937.

Xue et al. Drug-symptom networking: Linking drug-likeness screening to drugdiscovery. Pharmacological Research 103 (2016) 105-113. j ourna l h om epage: w ww.elsevier.com/locate/yphrs.

* cited by examiner

AUTOMATIC VALIDATION AND ENRICHMENT OF SEMANTIC RELATIONS BETWEEN MEDICAL ENTITIES FOR DRUG DISCOVERY

BACKGROUND

The present invention relates to techniques that provide identification of new compounds to be tested in drug discovery and of existing drugs in drug repurposing and of validating existing relations.

Conventionally, pharmaceutical drug development has been inefficient, with high expenditure but low productivity. Drug discovery, the process of identifying new drugs for treatment of diseases, is costly and time-consuming Candidate compounds must be identified, and lengthy and costly phases of testing must be performed.

Drug repositioning, the process of finding additional indications, such as diseases, etc., that may be treated with existing drugs, presents a promising avenue for identifying better and safer treatments without the full cost or time required for de novo drug development. Candidates for repositioning are usually either market drugs or drugs that have been discontinued in clinical trials for reasons other than safety concerns. Because the safety profiles of these drugs are known, clinical trials for alternative indications are cheaper, potentially faster and carry less risk than de novo drug development.

In both drug discovery and drug repositioning, finding compounds or existing drugs that have improved likelihoods of being effective is desirable. Semantic graphs are one technique that may be used for this. Existing semantic graphing solutions do not take into consideration some of the possible direct relations between medical entities, such as Drugs, Diseases, Symptoms, Side-effects, Genes, etc., in the semantic medical entities graph. For example, Drugs entities are usually connected to Diseases (for which they are indicated), Side-effects or Genes but none of the existing methods take into consideration the direct relation between Drugs and Symptoms.

Accordingly, a need arises for techniques that provide enrichment of semantic graphing with relations that can enable a higher resolution of the semantic relationships and enable a more accurate prediction of new relations in the graph.

SUMMARY

Embodiments of the present systems and methods may provide techniques that provide enrichment of semantic graphing with relations that can enable a higher resolution of the semantic relationships and enable a more accurate prediction of new relations in the graph. This may provide the capability for faster and cheaper identification of new compounds to be tested in drug discovery and of existing drugs in drug repurposing and of validating existing relations. Embodiments of the present systems and methods may utilize a novel type of direct relationship, which has a higher resolution of semantic relationship, and enables a more accurate prediction of additional relations in the semantic graph. Embodiments may use and enrich new knowledge-bases including a Drug-Treats-Symptom relationship knowledgebase and may also use a more sophisticated prediction method using a modification of Denoising Auto-Encoder (DAE).

For example, in an embodiment, a method for drug discovery and drug repositioning may be implemented in a computer system comprising a processor, memory accessible by the processor, and computer program instructions stored in the memory and executable by the processor, the method comprising: generating or adding to a database comprising information relating to symptoms treated by drugs, the information obtained based on data relating to a plurality of aspects of drugs and pharmaceutical compounds; generating or adding semantic relationships, at the computer system, based on the information in the database relating to symptoms treated by drugs, the generated semantic relationships represented in the form of a semantic graph; inferring, at the computer system, new relations among the semantic relationships in the semantic graph using Denoising Autoencoders to process the semantic graph; and generating, at the computer system, predictions for drug discovery and drug repositioning based on the semantic relationships, including the newly found relations.

In embodiments, the database may be generated or added to by: collecting, at the computer system, data relating to a plurality of aspects of drugs and pharmaceutical compounds; extracting, at the computer system, relevant terms from the collected data; and mapping, at the computer system, the extracted relevant terms to structured medical terms. The semantic relationships may be generated or added to by: generating, at the computer system, semantic relationships represented in the form of a semantic graph based on the mapped structured medical terms. The generated semantic graph may comprise nodes and edges between the nodes, the nodes representing entities including at least some of drugs or pharmaceutical compounds, diseases or conditions, and symptoms, and the edges representing relations between the nodes comprising a treats relation and at least some of a causes side effect relation, a has relation, and an indicated relation. The relations between the nodes may further comprise a probability of the relation or a score for the relation. The data relating to a plurality of aspects of drugs and pharmaceutical compounds may comprise at least some of structured and unstructured data from textual and non-textual sources, including audio sources, video sources, drug labels, medical and drug related databases, medical articles and books, medical health records, social media, internet forums, and tutorials (textual, audio, and video).

In an embodiment, a system may comprise a processor, memory accessible by the processor, and computer program instructions stored in the memory and executable by the processor to perform: generating or adding to a database comprising information relating to symptoms treated by drugs, the information obtained based on data relating to a plurality of aspects of drugs and pharmaceutical compounds; generating or adding semantic relationships, at the computer system, based on the information in the database relating to symptoms treated by drugs the generated semantic relationships represented in the form of a semantic graph; inferring new relations among the semantic relationships in the semantic graph using Denoising Autoencoders to process the semantic graph, and generating predictions for drug discovery and drug repositioning based on the semantic relationships, including the newly found relations, and validating existing relations.

In an embodiment, a computer program product for testing a software system, the computer program product comprising a non-transitory computer readable storage having program instructions embodied therewith, the program instructions executable by a computer, to cause the computer to perform a method comprising: generating or adding to a database comprising information relating to symptoms treated by drugs, the information obtained based on data relating to a plurality of aspects of drugs and pharmaceutical compounds; generating or adding semantic relationships, at the computer system, based on the information in the database relating to symptoms treated by drugs the generated semantic relationships represented in the form of a semantic graph; inferring, at the computer system, new relations among the semantic relationships in the semantic graph using Denoising Autoencoders to process the semantic graph, and generating, at the computer system, predictions for drug discovery and drug repositioning based on the semantic relationships, including the newly found relations.

BRIEF DESCRIPTION OF THE DRAWINGS

The details of the present invention, both as to its structure and operation, can best be understood by referring to the accompanying drawings, in which like reference numbers and designations refer to like elements.

DETAILED DESCRIPTION

Embodiments of the present systems and methods may provide techniques that provide enrichment of semantic graphing with relations that can enable a higher resolution of the semantic relationships and enable a more accurate prediction of new relations in the graph. This may provide the capability for faster and cheaper identification of new compounds to be tested in drug discovery and of existing drugs in drug repurposing and of validating existing relations. Embodiments of the present systems and methods may utilize a novel type of direct relationship, which has a higher resolution of semantic relationship, and enables a more accurate prediction of additional relations in the semantic graph. Embodiments may generate a new knowledgebase including a Drug-Treats-Symptom relationship, and may also use a more sophisticated prediction method using a modification of Denoising Auto-Encoder (DAE).

Figure 1:
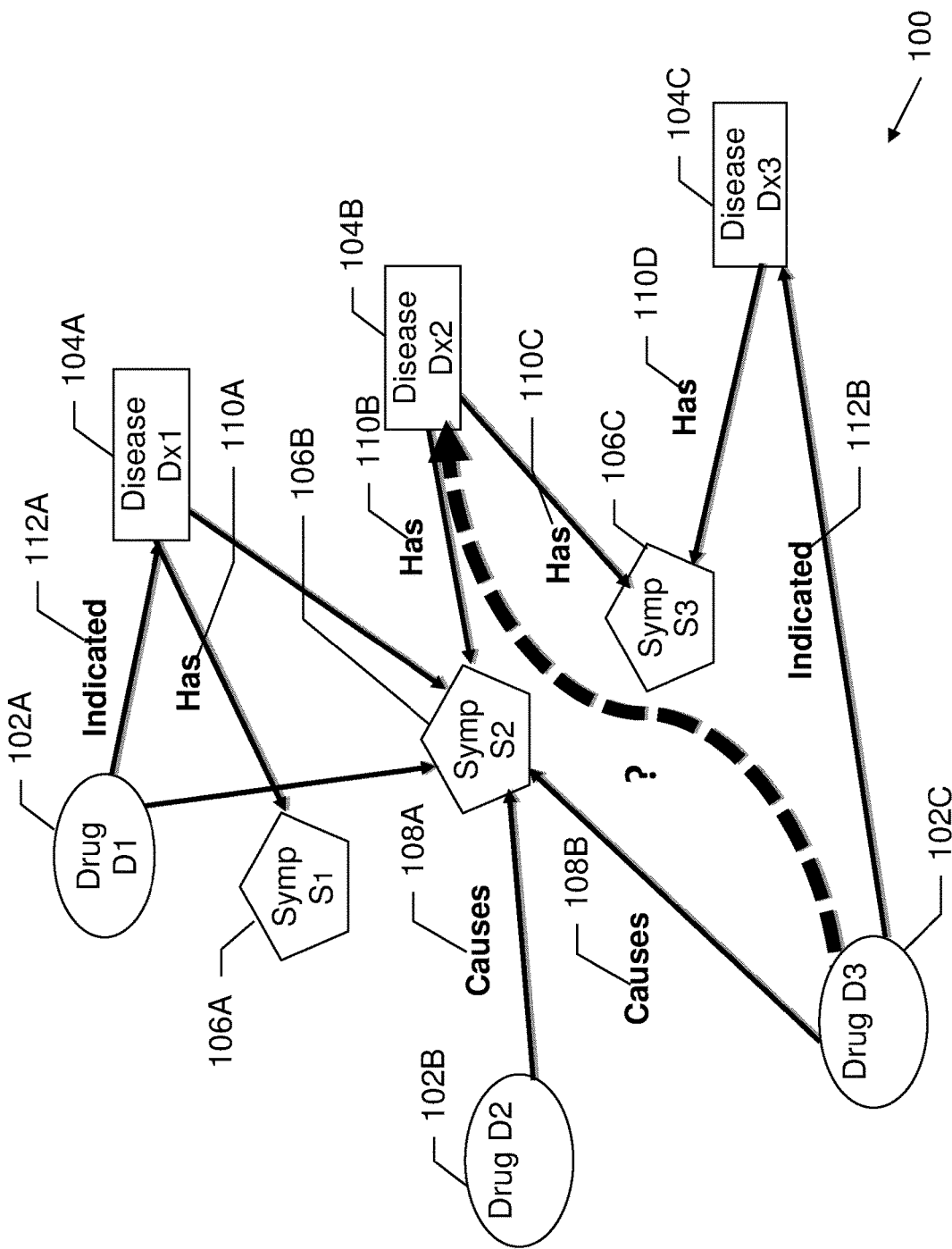
FIG. 1 illustrates an exemplary semantic graph with multiple medical entities according to embodiments of the present systems and methods.

An example of semantic graph 100 with multiple medical entities is shown in FIG. 1. Medical entities may include Drugs 102A-C, Diseases 104A-C, Symptoms 106A-C, Side-effects (not shown), Genes (not shown), etc. Semantic relations may include "Treats" (not shown) (for example, a drug treats a disease or a symptom), "Causes" 108A-B (for example, a drug causes a side effect), "Has" 110A-D (for example, a disease has symptoms), "Indicated" 112A-B (for example, a drug is approved for treating a disease), "Targets" (not shown) (for example, a drug targets a protein), etc. Embodiments of the present systems and methods may discover new semantic relations that could support drug discovery or drug repurposing, for example, between the entities Drugs and Diseases, such as Drug D is indicated to Disease Dx; or between drugs and proteins.

Embodiments of the present systems and methods may computationally suggest candidates for drug (or other medical treatments/procedures) repurposing or suggest therapeutic functionalities of new compounds.

Embodiments of the present systems and methods may predict new relations in the semantic graph of medical entities. Such relations may be translated into meaningful insights. For example, a new relation Drug-Treats-Disease means that an existing drug may be indicated to a new disease (drug repurposing) or Compound-Represses-Protein may help in the process of new drug discovery. In order to achieve this task, embodiments may use a new type of knowledgebase that translates into semantic relations that have not been used before: Drug-Treats-Symptom relationship. These new relations may enrich the knowledge embedded into the semantic graph and thus may help to increase the accuracy of novel predictions of new relations in the semantic graph of medical entities.

New Drug-Treats-Symptom relationships. Although drugs are indicated for diseases, many times diseases are characterized by several symptoms. The indicated drugs may not treat the root cause of the disease, but rather treat or ease specific symptoms (disease modifying vs. symptomatic drugs). Embodiments of the present systems and methods may enable finding new indications for existing drugs by generating and using the direct relationship between drugs and symptoms. If the direct effect of each drug on each symptom is known, additional data, such as drug-disease and disease-symptoms relationships, may be utilized in order to generate new disease candidates for existing drugs or to find new compounds functionalities. Likewise, embodiments may provide validation of existing relations, such as indications, causations, symptoms, etc. In embodiments, a database of Drug-Treats-Symptom relationships may be generated and used to enrich the semantic graph. The enrichment of the graph may be done, for example, through a novel modification of a Denoising Auto-Encoder (DAE). The input of the DAE may include all available knowledge encoded in the semantic graph, and the output may be translated into new relations in the graph, along with a confidence score.

Figure 2:
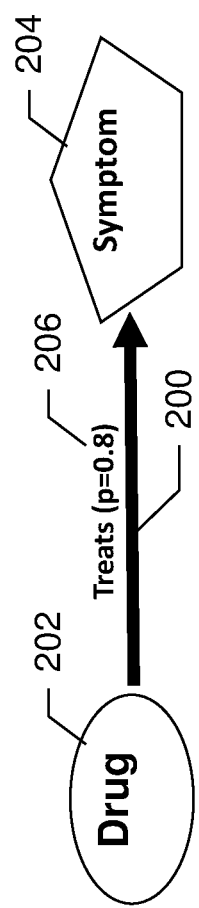
FIG. 2 is an exemplary diagram of a relation according to embodiments of the present systems and methods.

Embodiments of the present systems and methods may utilize and implement a relation 200 between Drug 202 and Symptoms 204, as shown in FIG. 2. Embodiments may also include a probability or score 206, which accompanies each relation. Embodiments may generate a baseline for this relation type and use it in order to predict new relations (that is, edges) in the graph.

Instead of observing a disease as a high-level homogenous condition, a disease may be viewed as a set of symptoms, where each drug may actually treat a subset of these symptoms. This approach enables the investigation of the actual effect of the drugs and enables a more accurate prediction of new relations based on the relevant symptom manifestation, which may be different even for patients with the same disease. In addition to causing side-effects or worsening existing conditions, the relationship between drugs and symptoms can be of "treats" or "reduces" (with or without targeting their cause). The relationships between drugs and symptoms may provide an additional resolution layer for understanding the underlined drugs mechanisms and thus may play an important role in the task of finding new semantic relations.

Generating a knowledgebase of Drug-Treats-Symptom relationships. Currently, there exist several databases that define various related relation types between medical entities. For example, the relationship between drugs and diseases is published by the FDA by providing drug indications based on clinical trials. The relationship between diseases and symptoms is sometimes used for identifying diseases from existing symptoms (for example, https://symptoms.webmd.com/) and also several publications have investigated this relation type (for example, https://www.nature.com/articles/ncomms5212 and https://ieeexploreleee.org/stamp/stamp.jsp?tp=&amumber=8122734). There are also other databases, such as The Human Phenotype Ontology (https://hpo.jax.org/), which maps the relationship between diseases and phenotypes, or KEGG Pathway Database, which maps the relationship between Metabolism, Genetics, Diseases, and Drugs (https://www.genome.jp/kegg/). The direct relationship between drugs and symptoms, however, has limited publicly available resources, except from databases that describe side-effects of drugs (for example, http://sideeffects.embl.de/), but not which symptoms are affected by each drug.

Figure 3:
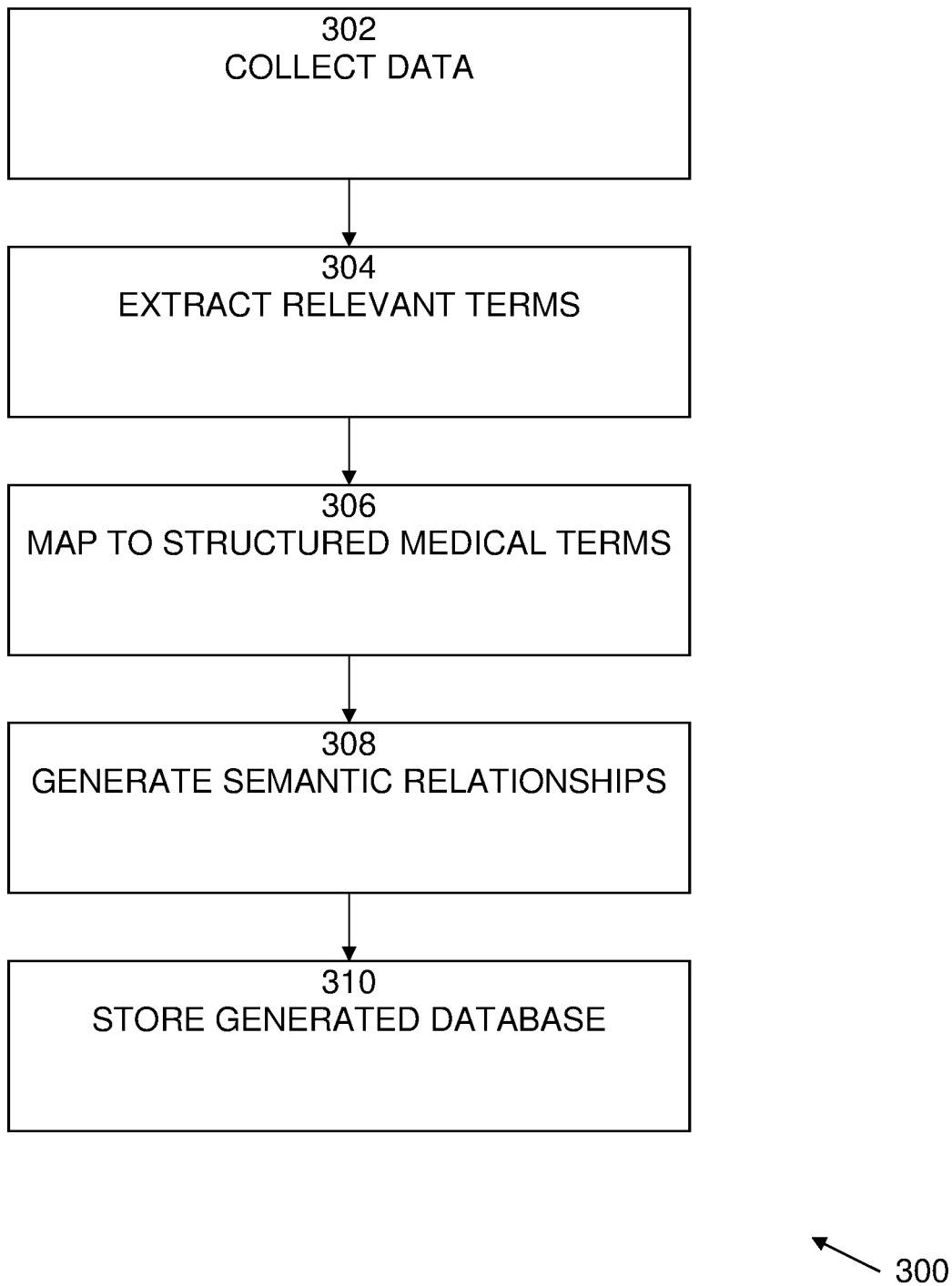
FIG. 3 is an exemplary flow diagram of a process of generating a database of Drug-Treats-Symptom relationships according to embodiments of the present systems and methods.

Embodiments may generate a database of Drug-Treats-Symptom relationships, which may be used to enrich the semantic graph of medical entities. An exemplary flow diagram of a process 300 of generating a database of Drug-Treats-Symptom relationships is shown in FIG. 3. Process 300 may begin with 302, in which data may be collected. For example, the collected data may include various structured and unstructured data from various textual and non-textual sources, such as audio & video, sources such as drug labels, medical and drug related databases, medical articles and books, medical health records, social media, internet forums, tutorials (textual, audio, and video), etc. These resources (and others), may be used to enrich the potential pool of data that may be used for extraction, analysis, and generation of Drug-Treats-Symptom relationships. At 304, known processes may be used for the text, audio, and image analysis in order to extract relevant terms such as drug names, symptoms, diseases and the relations between them. At 306, the extracted terms may be mapped to structured medical terms and ontologies, such as MeSH terms, ICD, or RxNorm, etc.

At 308, the terms may be analyzed (in the context of the data sources described above) in order to generate semantic relationships between them. Examples may include:

Sentiment text analysis that may be used for understanding whether a drug "causes" or "treats" a specific symptom.

Terms co-occurrences may be used to generate a weighted graph where nodes are terms and edge weights are the co-occurrence of the two nodes. Graph features and structure may be analyzed in order to find semantic relations between nodes.

Word embeddings, for example, using word2vec (a group of related models that are used to produce word embeddings, as described in U.S. Pat. No. 9,037,464) or GloVe (Global Vectors, a model for distributed word representation, from Stanford University), may be used to infer the relatedness of two terms, for example "Drug A is to Symptom X as Drug B is to Symptom Y" etc.

At 310, the generated database may be stored. The generated database may include a set of relations between drugs and symptoms where each relation includes a direction of the effect (e.g., "causes" or "treats") and a confidence level. The generated database may include a new knowledgebase that includes Drug-Treats-Symptom relations in a structured manner and is generated as described above. After generating this knowledgebase, these relations may be encoded in a semantic graph. Further, Denoising Autoencoders (DAE) may be used for the prediction task, such as drug discovery, where the DAE may also use the encoded drug-treats-symptom relations as generated previously. These relations may also be enriched using the DAE.

As mentioned above, DAE may be used to predict new relations. A classic usage of DAE is to generate a latent compact representation of a single domain by unsupervised reconstruction of the input. By randomly deleting part of the input and trying to reconstruct the full input, the network learns the complex relationships between the input nodes in order to reconstruct the full input from its partial information.

In embodiments of the present systems and methods, a modified version of DAE may be used. A denoising autoencoder (DAE) is a particular type of autoencoder, and may be considered to be a type of deep neural network. The DAE may be trained to use a hidden layer to generate a particular model based on its inputs. In general, autoencoders may reconstruct their inputs using, for example, unsupervised machine learning, and may obtain results from unstructured data. In order to match target outputs to inputs and reach an equilibrium, DAEs may accept a corrupted version of an input, and may attempt to reconstruct a clean input through the use of denoising techniques. Noise may be introduced in a specific amount as a percentage of the input size, which may force the hidden layer to produce a clean version from the corrupted version. DAEs may also be stacked on each other to provide iterative learning to achieve their goal.

Figure 4:
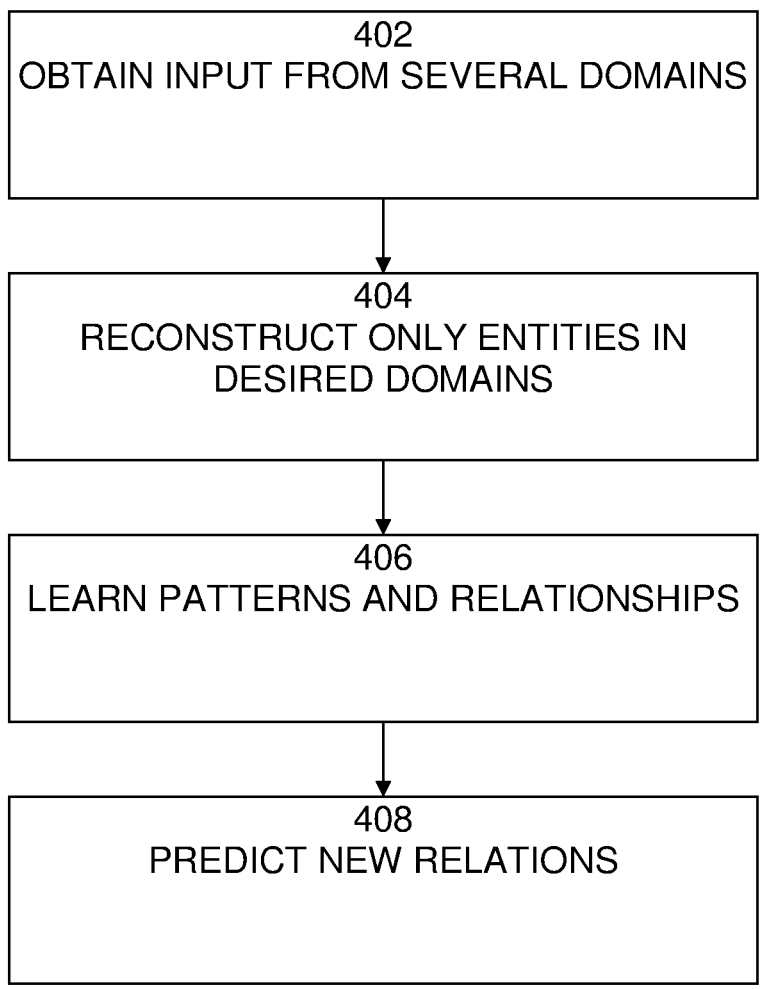
FIG. 4 is an exemplary flow diagram of a process of Denoising Autoencoders according to embodiments of the present systems and methods.

An exemplary process of DAE 400 is shown in FIG. 4. At 402, input from several domains, such as Drugs side-effects, Drug Indications, Fingerprints etc., may be obtained, rather than input from just one domain. At 404, reconstruction of only entities for which discovery of new relations is desired may be performed. For example, as noted, a possible embodiment of the semantic graph enrichment is Drug repurposing.

Figure 5:
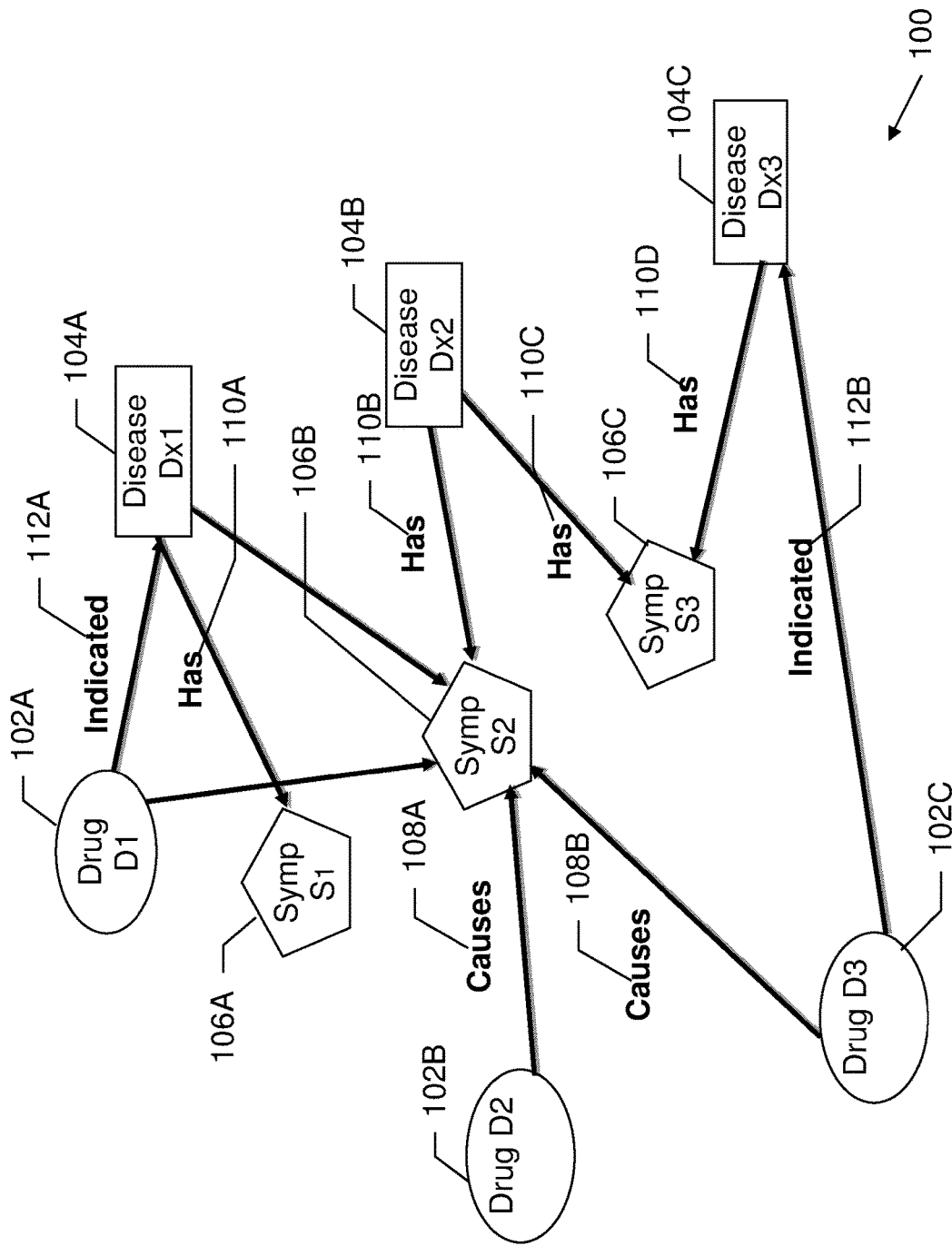
FIG. 5 is an exemplary diagram of learning patterns and relationships according to embodiments of the present systems and methods.

At 406, patterns and relationships may be learned. For example, as shown in FIG. 5, each Drug 102A-C may be represented by one or more numerical vectors, where the value of each entry represents a semantic relation between the drug and some other medical entity as encoded in the semantic graph. For example, in FIG. 5, Drug D1 vector entry corresponding to its "Indicated" relation with Disease Dx1 112A may be set to True, Drug D2 vector entry corresponding to "Causes (side-effect)" with Symptom S2 108A may be set to True, and Drug D3 vector entry corresponding to "Causes (side-effect)" with Symptom S2 108B and "Indicated" with Disease Dx3 112B may be set to True; while vector entries corresponding to non-existing edges may be set to False.

Figure 6:
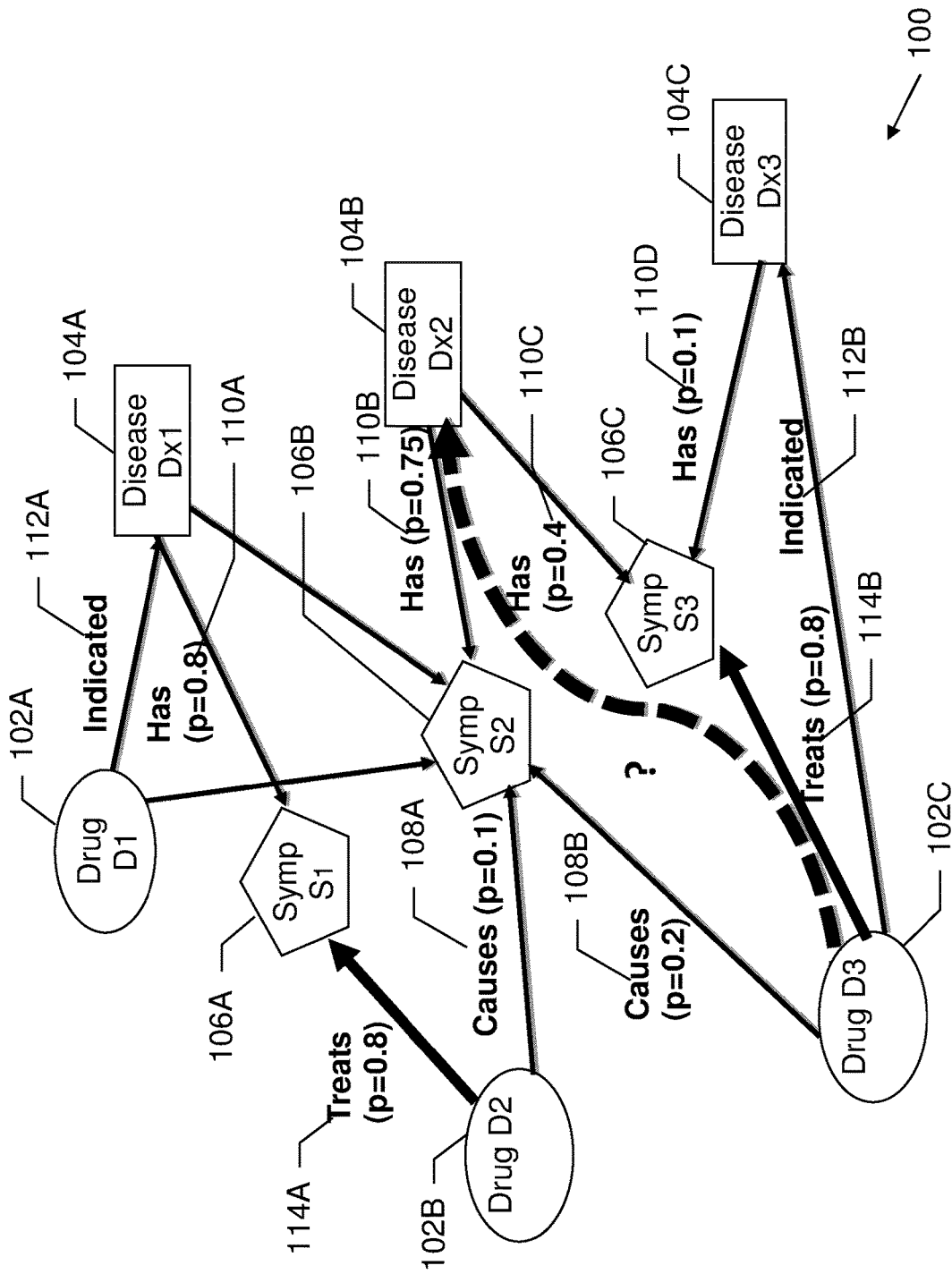
FIG. 6 is an exemplary diagram of edge values according to embodiments of the present systems and methods.
Figure 7:
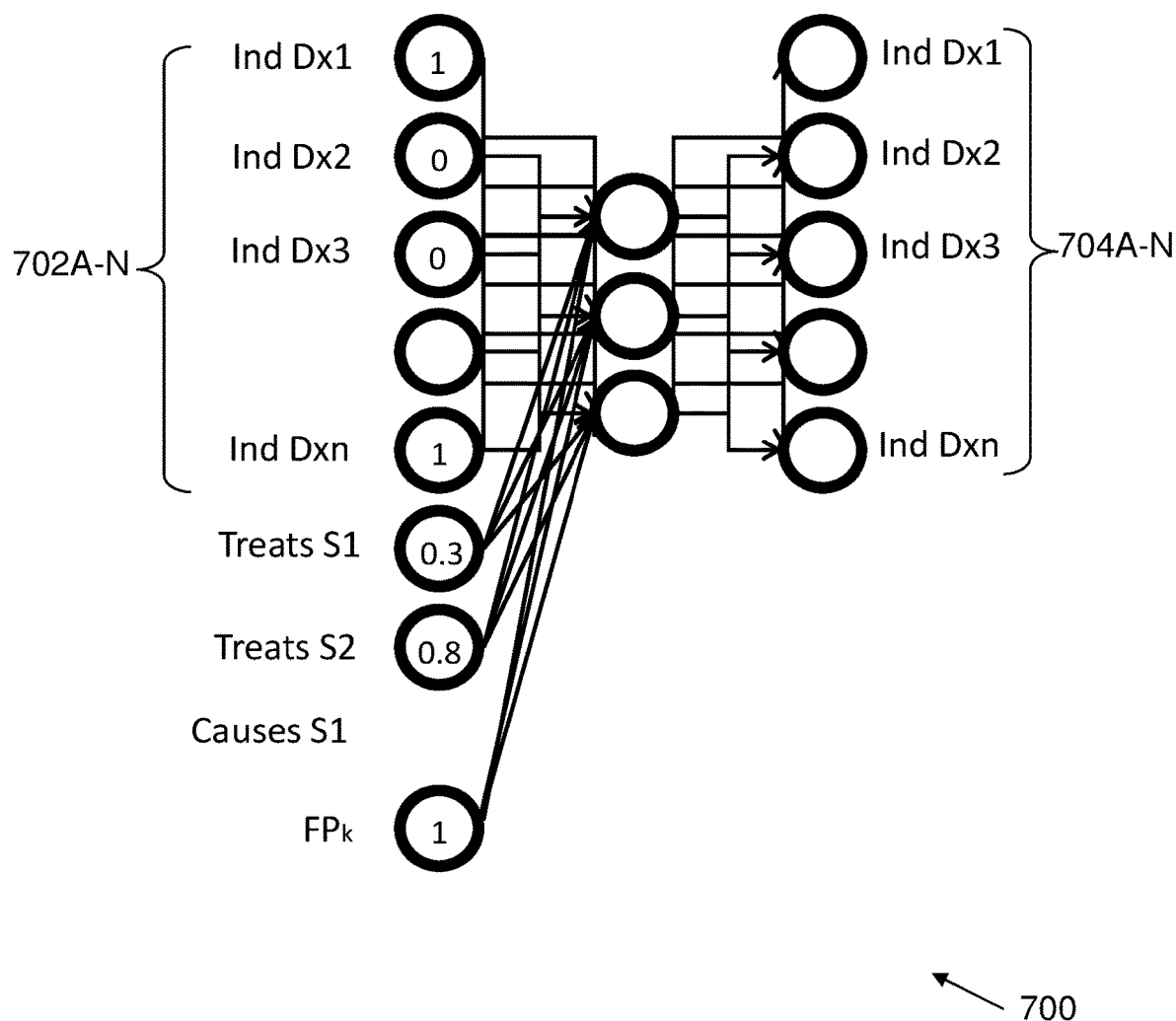
FIG. 7 is an exemplary diagram of an output of a network according to embodiments of the present systems and methods.

As shown in the example of FIG. 6, the vector value may be either binary (for example, True or False for the "Indicated" relation, such as "Indicated" relations 112A-B) or a probability (for example, the "Causes side-effect" relation, such as "Causes side-effect" relations 108A-B) but may also be any appropriate score. In addition, the "Treats" relation, such as "Treats" relations 114A-B may be included in the graph 100. The output of the network may be either a subset or a different set of relations, for example input nodes "Indicated to Disease Dx" relations 702A-N may be mapped to output nodes 704A-N, as shown in FIG. 7. By employing an unsupervised training scheme, the DAE learns the complicated patterns of the existing relationship in order to recover the output, by randomly deleting values from the input nodes. Unlike classic DAE, the output nodes may not be identical to the input nodes.

At 408, by learning complex patterns and relationships between the nodes of the input vector, the DAE may predict new relations in the graph, for example, of the form "Drug D is indicated to Disease Dx". After training the network, the trained network may be used to generate the actual final predictions using the full input information. New predictions may be examined according to their confidence level by using, for example, a Softmax function in the last layer. Softmax extends the idea of single-class logistic regression into a multi-class world. That is, Softmax assigns decimal probabilities to each class in a multi-class problem. Those decimal probabilities must add up to 1.0. This additional constraint helps training converge more quickly than it otherwise would. Softmax is implemented through a neural network layer just before the output layer. The Softmax layer must have the same number of nodes as the output layer.

Figure 8:
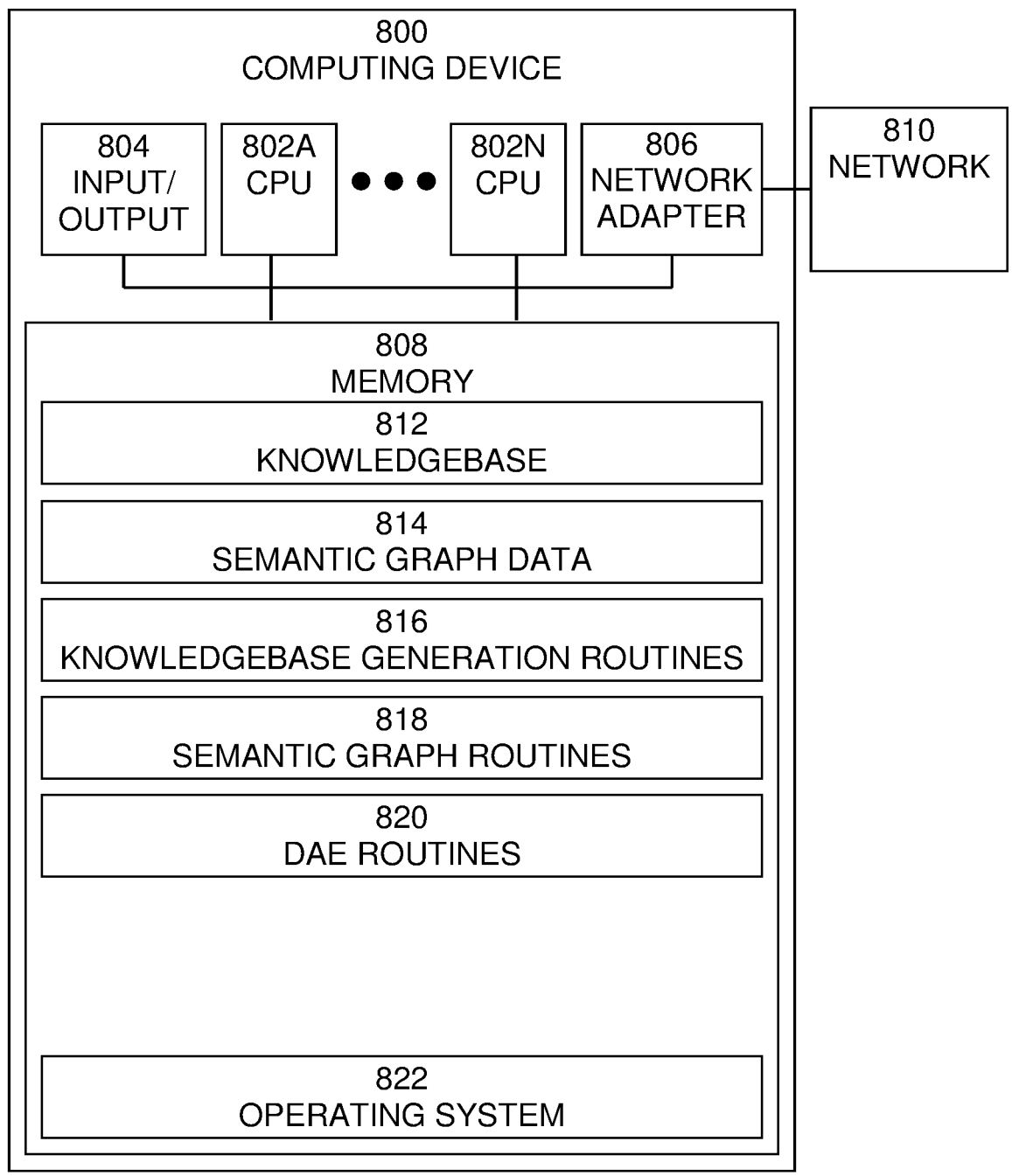
FIG. 8 is an exemplary block diagram of a computer system, in which processes involved in the embodiments described herein may be implemented.

An exemplary block diagram of a computer system 800, in which processes involved in the embodiments described herein may be implemented, is shown in FIG. 8. Computer system 800 may be implemented using one or more programmed general-purpose computer systems, such as embedded processors, systems on a chip, personal computers, workstations, server systems, and minicomputers or mainframe computers, or in distributed, networked computing environments. Computer system 800 may include one or more processors (CPUs) 802A-802N, input/output circuitry 804, network adapter 806, and memory 808. CPUs 802A-802N execute program instructions in order to carry out the functions of the present communications systems and methods. Typically, CPUs 802A-802N are one or more microprocessors, such as an INTEL CORE® processor. FIG. 8 illustrates an embodiment in which computer system 800 is implemented as a single multi-processor computer system, in which multiple processors 802A-802N share system resources, such as memory 808, input/output circuitry 804, and network adapter 806. However, the present communications systems and methods also include embodiments in which computer system 800 is implemented as a plurality of networked computer systems, which may be single-processor computer systems, multi-processor computer systems, or a mix thereof.

Input/output circuitry 804 provides the capability to input data to, or output data from, computer system 800. For example, input/output circuitry may include input devices, such as keyboards, mice, touchpads, trackballs, scanners, analog to digital converters, etc., output devices, such as video adapters, monitors, printers, etc., and input/output devices, such as, modems, etc. Network adapter 806 interfaces device 800 with a network 810. Network 810 may be any public or proprietary LAN or WAN, including, but not limited to the Internet.

Memory 808 stores program instructions that are executed by, and data that are used and processed by, CPU 802 to perform the functions of computer system 800. Memory 808 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 808 may vary depending upon the function that computer system 800 is programmed to perform. In the example shown in FIG. 8, exemplary memory contents are shown representing routines and data for embodiments of the processes described above. However, one of skill in the art would recognize that these routines, along with the memory contents related to those routines, may not be included on one system or device, but rather may be distributed among a plurality of systems or devices, based on well-known engineering considerations. The present systems and methods may include any and all such arrangements.

In the example shown in FIG. 8, memory 808 may include knowledgebase 812, semantic graph data 814, knowledgebase generation routines 816, semantic graph routines 818, DAE routines 820, and operating system 822. Knowledgebase 812 may include data relating to relationships between drugs, pharmaceutical compounds, symptoms, side effects, etc., as described above. Semantic graph data 814 may include data representing semantic graphs of relationships between drugs, compounds, symptoms, side effects, etc., as described above. Knowledgebase generation routines 816 may include software routines to generate knowledgebase 812 from data relating to a plurality of aspects of drugs and pharmaceutical compounds, as described above. Semantic graph routines 818 may include software routines to generate and/or enrich a semantic graph of the medical entities, as described above. DAE routines 820 may include software routines to predict new relations and/or enrich relations using DAE, as described above. Operating system 822 may provide overall system functionality.

As shown in FIG. 8, the present communications systems and methods may include implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multi-tasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A method for drug discovery and drug repositioning, implemented in a computer system comprising a processor, memory accessible by the processor, and computer program instructions stored in the memory and executable by the processor, the method comprising:
  generating or adding to a database comprising information relating to symptoms treated by drugs, the information obtained based on data relating to a plurality of aspects of drugs and pharmaceutical compounds;
  generating or adding semantic relationships, at the computer system, based on the information in the database relating to symptoms treated by drugs, the generated semantic relationships represented in the form of a semantic graph;
  using a Denoising Autoencoder to learn, at the computer system, new patterns, and relationships among the semantic relationships in the semantic graph, wherein the Denoising Autoencoder comprises a deep neural network, and the Denoising Autoencoder is trained to use a hidden layer to generate a particular model based on its inputs; and
  using the Denoising Autoencoder to generate, at the computer system, predictions for drug discovery and drug repositioning based on the semantic relationships, including the newly found relations, based on the learned new patterns and relationships.

2. The method of claim 1, wherein the database is generated or added to by:
  collecting, at the computer system, data relating to a plurality of aspects of drugs and pharmaceutical compounds;
  extracting, at the computer system, relevant terms from the collected data; and
  mapping, at the computer system, the extracted relevant terms to structured medical terms.

3. The method of claim 2, wherein the semantic relationships are generated or added to by:
  generating, at the computer system, semantic relationships represented in the form of a semantic graph based on the mapped structured medical terms.

4. The method of claim 3, wherein the generated semantic graph comprises nodes and edges between the nodes, the nodes representing entities including at least some of drugs or pharmaceutical compounds, diseases or conditions, and symptoms, and the edges representing relations between the nodes comprising a treats relation and at least some of a causes side effect relation, a has relation, and an indicated relation.

5. The method of claim 4, wherein the relations between the nodes further comprise a probability of the relation or a score for the relation.

6. The method of claim 5, wherein the data relating to a plurality of aspects of drugs and pharmaceutical compounds comprises at least some of structured and unstructured data from textual and non-textual sources, including audio sources, video sources, drug labels, medical and drug related databases, medical articles and books, medical health records, social media, internet forums, and tutorials (textual, audio, and video).

7. A system for testing a software system, the system comprising a processor, memory accessible by the processor, and computer program instructions stored in the memory and executable by the processor to perform:
  generating or adding to a database comprising information relating to symptoms treated by drugs, the information obtained based on data relating to a plurality of aspects of drugs and pharmaceutical compounds;
  generating or adding semantic relationships, at the computer system, based on the information in the database relating to symptoms treated by drugs, the generated semantic relationships represented in the form of a semantic graph;
  using a Denoising Autoencoder to learn, at the computer system, new patterns, and relationships among the semantic relationships in the semantic graph, wherein the Denoising Autoencoder comprises a deep neural network, and the Denoising Autoencoder is trained to use a hidden layer to generate a particular model based on its inputs; and
  using the Denoising Autoencoder to generate, at the computer system, predictions for drug discovery and drug repositioning based on the semantic relationships, including the newly found relations, based on the learned new patterns and relationships.

8. The system of claim 7, wherein the database is generated or added to by:
  collecting, at the computer system, data relating to a plurality of aspects of drugs and pharmaceutical compounds;
  extracting, at the computer system, relevant terms from the collected data; and
  mapping, at the computer system, the extracted relevant terms to structured medical terms.

9. The system of claim 8, wherein the semantic relationships are generated or added to by:
  generating, at the computer system, semantic relationships represented in the form of a semantic graph based on the mapped structured medical terms.

10. The system of claim 9, wherein the generated semantic graph comprises nodes and vectors between the nodes, the nodes representing entities including at least some of drugs or pharmaceutical compounds, diseases or conditions, and symptoms, and the edges representing relations between the nodes comprising a treats relation and at least some of a causes side effect relation, a has relation, and an indicated relation.

11. The system of claim 10, wherein the relations between the nodes further comprise a probability of the relation or a score for the relation.

12. The system of claim 11, wherein the data relating to a plurality of aspects of drugs and pharmaceutical compounds comprises at least some of structured and unstructured data from textual and non-textual sources, including audio sources, video sources, drug labels, medical and drug related databases, medical articles and books, medical health records, social media, internet forums, and tutorials (textual, audio, and video).

13. A computer program product for testing a software system, the computer program product comprising a non-transitory computer readable storage having program instructions embodied therewith, the program instructions executable by a computer, to cause the computer to perform a method comprising:
  generating or adding to a database comprising information relating to symptoms treated by drugs, the information obtained based on data relating to a plurality of aspects of drugs and pharmaceutical compounds;

generating or adding semantic relationships, at the computer system, based on the information in the database relating to symptoms treated by drugs, the generated semantic relationships represented in the form of a semantic graph;

using a Denoising Autoencoder to learn, at the computer system, new patterns, and relationships among the semantic relationships in the semantic graph, wherein the Denoising Autoencoder comprises a deep neural network, and the Denoising Autoencoder is trained to use a hidden layer to generate a particular model based on its inputs; and using the Denoising Autoencoder to generate, at the computer system, predictions for drug discovery and drug repositioning based on the semantic relationships, including the newly found relations, based on the learned new patterns and relationships.

14. The computer program product of claim 13, wherein the database is generated or added to by:

collecting, at the computer system, data relating to a plurality of aspects of drugs and pharmaceutical compounds;

extracting, at the computer system, relevant terms from the collected data; and mapping, at the computer system, the extracted relevant terms to structured medical terms.

15. The computer program product of claim 14, wherein the semantic relationships are generated or added to by:

generating, at the computer system, semantic relationships represented in the form of a semantic graph based on the mapped structured medical terms.

16. The computer program product of claim 15, wherein the generated semantic graph comprises nodes and vectors between the nodes, the nodes representing entities including at least some of drugs or pharmaceutical compounds, diseases or conditions, and symptoms, and the edges representing relations between the nodes comprising a treats relation and at least some of a causes side effect relation, a has relation, and an indicated relation.

17. The computer program product of claim 16, wherein the relations between the nodes further comprise a probability of the relation or a score for the relation.

18. The computer program product of claim 17, wherein the data relating to a plurality of aspects of drugs and pharmaceutical compounds comprises at least some of structured and unstructured data from textual and non-textual sources, including audio sources, video sources, drug labels, medical and drug related databases, medical articles and books, medical health records, social media, internet forums, and tutorials (textual, audio, and video).

* * * * *